United States Patent
Sands

(10) Patent No.: US 11,351,092 B2
(45) Date of Patent: Jun. 7, 2022

(54) SYSTEM AND METHOD FOR MIXING AND DELIVERING A SOLUTION

(71) Applicant: John C. Sands, Fuquay Varina, NC (US)

(72) Inventor: John C. Sands, Fuquay Varina, NC (US)

( * ) Notice: Subject to any disclaimer, the term of this patent is extended or adjusted under 35 U.S.C. 154(b) by 529 days.

(21) Appl. No.: 16/422,188

(22) Filed: May 24, 2019

(65) Prior Publication Data
US 2020/0188230 A1    Jun. 18, 2020

Related U.S. Application Data

(63) Continuation-in-part of application No. 16/223,024, filed on Dec. 17, 2018, now Pat. No. 10,307,336.

(51) Int. Cl.
*A61J 1/20*      (2006.01)
*A61M 5/178*   (2006.01)

(52) U.S. Cl.
CPC ............. *A61J 1/2093* (2013.01); *A61J 1/201* (2015.05); *A61J 1/2096* (2013.01); *A61M 5/1782* (2013.01)

(58) Field of Classification Search
CPC ........ A61J 1/201; A61J 1/2027; A61J 1/2093; A61J 1/2096; A61M 5/1782; A61M 5/282;

(Continued)

(56) References Cited

U.S. PATENT DOCUMENTS 2,721,552 A * 10/1955 Nosik ................. F42B 3/00
                                                         206/222
4,615,437 A    10/1986 Finke et al.
(Continued)

FOREIGN PATENT DOCUMENTS

| JP | 2004097583 A | 4/2004 |
| WO | 2005030111 A1 | 4/2005 |
| WO | 2007058866 A1 | 5/2007 |

OTHER PUBLICATIONS

ISA/EP; International Search Report and Written Opinion for International Patent Application No. PCT/US2019/066144 dated Mar. 19, 2020, 18 pages.
WIPO; International Preliminary Report on Patentability for International Patent Application No. PCT/US2019/066144 dated Jul. 1, 2021, 9 pages.

*Primary Examiner* — Benjamin J Klein
(74) *Attorney, Agent, or Firm* — NK Patent Law

(57) ABSTRACT

A device for mixing and delivering a solution includes a tubular barrel that includes a first end, a second end, and interior compartment. A first plunger is positionable at the first end of the barrel, is moveable within the interior compartment of the barrel, and includes a spike protruding into the interior compartment, the spike having an end configured for piercing a membrane. A second plunger is positionable within the barrel, is also moveable within the interior compartment of the barrel, and has a pierceable membrane. The second plunger and the second end form a first area within the barrel for housing a first solution to be mixed and the first and second plungers form a second area within the barrel for housing a second solution to be mixed. The first and second plungers are slidably arranged within the interior area of the tubular barrel such that moving the first plunger toward the second plunger causes the spike to pierce the pierceable membrane and push the second solution through the pierced membrane to mix with the first solution in the first area.

18 Claims, 8 Drawing Sheets

(58) Field of Classification Search
CPC .... A61M 5/284; A61M 5/288; A61M 5/3134; A61M 5/31596
See application file for complete search history.

(56) References Cited

U.S. PATENT DOCUMENTS

| | | | | |
|---|---|---|---|---|
| 4,781,679 A * | 11/1988 | Larkin | ............... | A61J 1/2089 604/413 |
| 5,352,196 A * | 10/1994 | Haber | ............... | A61J 1/2089 206/221 |
| 5,360,410 A * | 11/1994 | Wacks | ............... | A61M 5/20 604/110 |
| 5,476,449 A * | 12/1995 | Richmond | ........ | A61M 5/31596 604/191 |
| 5,603,695 A | 2/1997 | Erickson | | |
| 5,637,087 A * | 6/1997 | O'Neil | ............... | A61M 5/282 604/82 |
| 5,950,817 A | 9/1999 | Sellars et al. | | |
| 6,387,074 B1 * | 5/2002 | Horppu | ............... | A61M 5/2066 604/89 |
| 6,723,074 B1 * | 4/2004 | Halseth | ............... | A61M 5/284 604/191 |
| 7,470,258 B2 * | 12/2008 | Barker | ............... | A61M 5/3234 604/192 |
| 8,142,403 B2 * | 3/2012 | Carlyon | ............ | A61M 5/31596 604/191 |
| 9,055,992 B2 * | 6/2015 | Larson | ............... | A61M 5/285 |
| 2006/0178644 A1 * | 8/2006 | Reynolds | ........... | A61M 5/31511 604/232 |
| 2008/0171971 A1 * | 7/2008 | DiPerna | ............. | A61M 5/31596 604/82 |
| 2018/0200443 A1 * | 7/2018 | Keadle | ............... | A61M 5/2448 |
| 2018/0344933 A1 * | 12/2018 | Dittrich | ............. | A61M 5/31596 |
| 2020/0375847 A1 * | 12/2020 | Frame | ................ | A61J 1/2096 |

* cited by examiner

SYSTEM AND METHOD FOR MIXING AND DELIVERING A SOLUTION

RELATED APPLICATIONS

This application is a continuation-in-part of U.S. patent application Ser. No. 16/223,024, titled "SYSTEM AND METHOD FOR MIXING AND DELIVERING A SOLUTION," filed on Dec. 17, 2018, the entire disclosure of which is here incorporated by reference.

TECHNICAL FIELD

The presently disclosed subject matter relates to a system and method for mixing and delivering a solution, such as buffered anesthetics.

BACKGROUND

Local anesthetics have been used for decades to decrease and/or eliminate the perception of pain to a patient. Local anesthetics function by blocking an ion channel upstream of a particular triggered nerve to impede all signals (e.g., pain) to the patient's brain. Local anesthetics are typically acidified to a pH of about 3.5 to 4.5 to increase stability, resulting in a longer shelf life. Once administered, the body of the patient must buffer the local anesthetic to a pH of 7.4 (the pH of the body) before the full effectiveness or numbness of the local anesthetic is achieved, which can take up to 20 minutes. Further, administering an acidic local anesthetic into human tissues creates a painful or burning sensation. Changing the pH of a local anesthetic to more closely mimic the pH of human tissue has been found to significantly decrease injection-associated pain. However, current methods of buffering local anesthetics are wasteful, time consuming, and expensive. Further, current methods are non-standardized, leaving room for human error. Particularly, physicians typically mix sodium carbonate (pH 8.4) with a desired local anesthetic at a ratio of 9:1 anesthetic to sodium bicarbonate by drawing a desired amount from larger vials of solution. Such a method is unmeasured and non-standardized. In addition, each large vial of buffered anesthetic solution is intended for a single patient, and is discarded after use. The physician will therefore discard the wasted solution or continue to use the vials on future patients, risking cross contamination. It would therefore be beneficial to provide a system and method that overcomes the shortcomings of the prior art.

SUMMARY

In some embodiments, the presently disclosed subject matter is directed to a device for mixing and delivering a solution. Particularly, the device includes a tubular barrel that includes a first end, a second end, and interior compartment. A first plunger is positionable at the first end of the barrel, is moveable within the interior compartment of the barrel, and includes a spike protruding into the interior compartment, the spike having an end configured for piercing a membrane. A second plunger is positionable within the barrel, is also moveable within the interior compartment of the barrel, and has a pierceable membrane. The second plunger and the second end form a first area within the barrel for housing a first solution to be mixed and the first and second plungers form a second area within the barrel for housing a second solution to be mixed. The first and second plungers are slidably arranged within the interior area of the tubular barrel such that moving the first plunger toward the second plunger causes the spike to pierce the pierceable membrane and push the second solution through the pierced membrane to mix with the first solution in the first area.

In some embodiments, the presently disclosed subject matter is directed to method of mixing and delivering a solution. First and second solutions to be mixed are housed within a tubular barrel having a first end, a second end, and interior compartment. A first plunger is moved within the barrel from a first end of the barrel toward a second plunger positioned within the barrel, wherein the second plunger and the second end form a first area within the barrel for housing the first solution and the first and second plungers form a second area within the barrel for housing a second solution to be mixed. Contact by the first plunger against the second plunger is caused, wherein the contact causes a spike on the first plunger to pierce a membrane on the second plunger and push the second solution through the pierced membrane to mix with the first solution in the first area; and moving the first and second plungers together within the barrel into the first area.

In some embodiments, the first solution is a local anesthetic solution. In some embodiments, the local anesthetic solution is selected from one or more of articaine, bupivacaine, carticaine, cinchocaine/dibucaine, etidocaine, levobupivacaine, lidocaine/lignocaine, mepivacaine, piperocaine, prilocaine, ropivacaine, trimecaine, procaine/benzocaine, chloroprocaine, cyclomethycaine, dimethocaine/larocaine, propoxycaine, procaine/novocaine, proparacaine, tetracaine/amethocaine, lidocaine/prilocaine, saxitoxin, tetrodotoxin, and pharmaceutically acceptable salts thereof.

In some embodiments, the second solution is a buffer. In some embodiments, the buffer is selected from one or more of sodium bicarbonate, potassium carbonate, calcium carbonate, ammonium carbonate, and magnesium carbonate.

In some embodiments, the plunger comprises a main body with an exterior cross-sectional circumference that is approximately equal to the interior cross-sectional circumference of the barrel.

In some embodiments, at least a portion of the barrel is transparent.

In some embodiments, the main body of the plunger comprises one or more sealing ribs.

In some embodiments, the container membrane is frangible. In some embodiments, the container membrane comprises one or more weakened areas comprising perforations, thinner material, or both.

BRIEF DESCRIPTION OF THE DRAWINGS

The previous summary and the following detailed descriptions are to be read in view of the drawings, which illustrate some (but not all) embodiments of the presently disclosed subject matter.

FIG. 1b is a cross-sectional side view of the device of FIG. 1a.

DETAILED DESCRIPTION

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a carpule" can include a plurality of such carpules, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

Figure 1A:
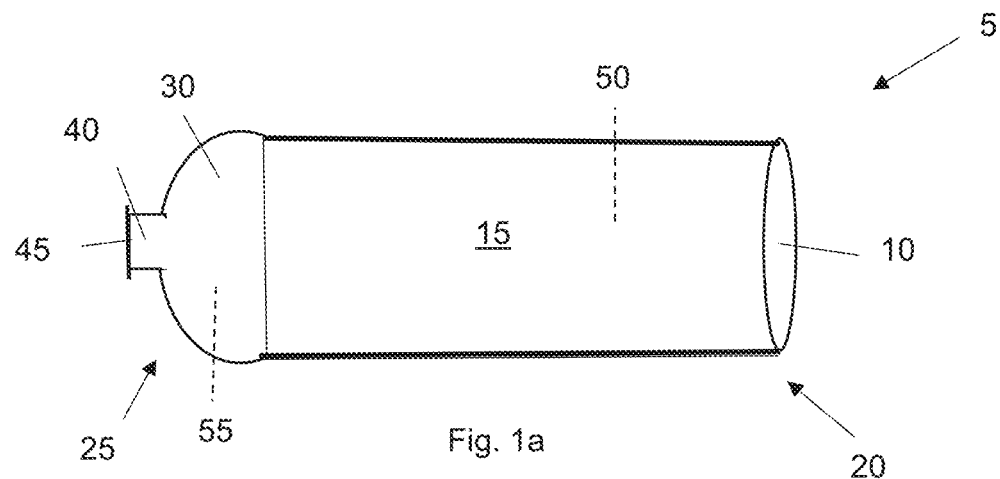
FIG. 1a is side plan view a device that can be used to mix and deliver first and second solutions in accordance with some embodiments of the presently disclosed subject matter.
Figure 1B:
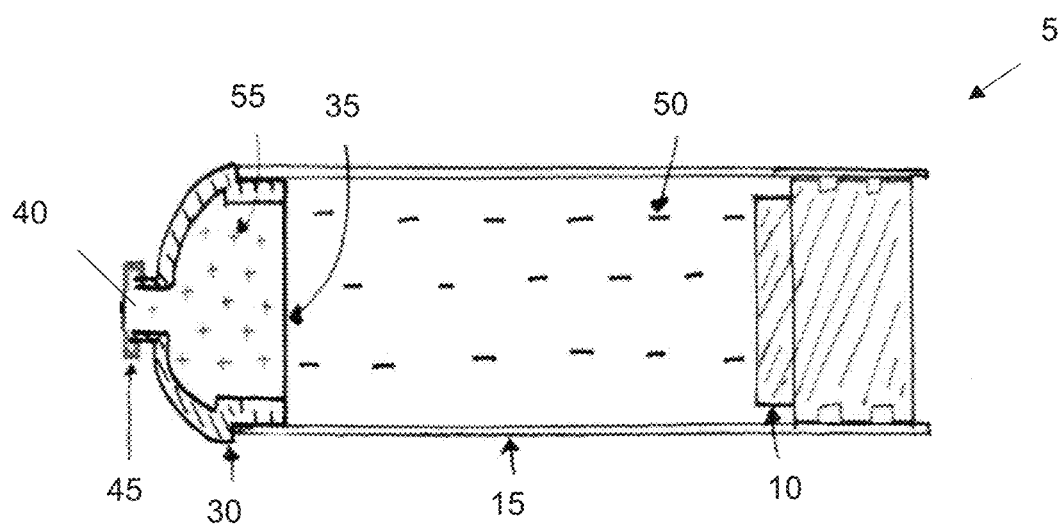

The presently disclosed subject matter is directed to a device for dispensing a mixture of a first composition (e.g., a drug) and a second composition (e.g., a diluent buffer, a second drug, or a solution). FIGS. 1a and 1b illustrate one embodiment of device 5 comprising plunger 10 that slidably engages with the interior of device barrel 15 at first end 20. Second end 25 of the device barrel includes flexible container 30 configured to house one or more solutions (e.g., sodium bicarbonate). Container 30 comprises membrane 35 positioned adjacent to the interior of the barrel, and exterior opening 40 facing the exterior environment. Opening 40 is covered by cap 45. First solution 50 (e.g., a local anesthetic) is housed within the interior of barrel 15, and second solution 55 (e.g., a buffer) is housed within the interior of container 30. As described in more detail herein below, the two solutions can be mixed on demand as needed by a physician to provide a buffered anesthetic solution. It should be appreciated that the presently disclosed subject matter is not limited, and the first and second solutions can be any two solutions (or powders) that are to be mixed on demand.

In some embodiments, device 5 is a carpule mixing device. The term "carpule" refers to a container, such as a vial, cartridge, or the like, generally made of glass and adapted to house a dose of a medical fluid. The carpule can be inserted into a syringe for dispensing (e.g., injecting) into a patient. Carpules typically include a puncturable cap on one end and a sliding plug on the other end. The cap can be punctured by the tip of a needle assembly of a carpule syringe to allow the fluid housed within the carpule to be dispensed. The plug is advanced towards the cap end of the carpule via a syringe plunger.

Figure 2:
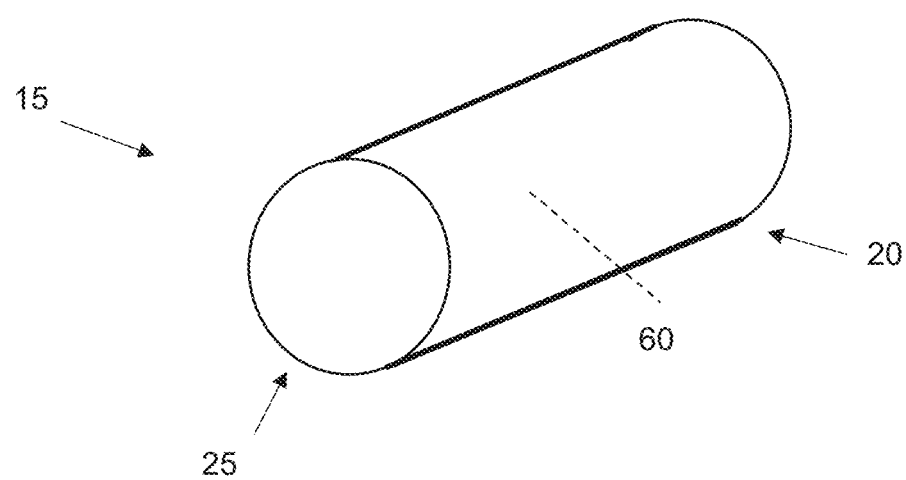
FIG. 2 is a perspective view of a barrel in accordance with some embodiments of the presently disclosed subject matter.

FIG. 2 illustrates one embodiment of barrel 15 that can be used with device 5. As shown, in some embodiments, the barrel can be configured in a cylindrical shape with hollow interior 60 and open ends 20, 25. However, the presently disclosed subject matter is not limited and the barrel can have any desired shape. The hollow interior of the barrel allows the movement of a plunger from first end 20 to second end 25. In this way, fluid housed within the barrel can be dispensed.

Barrel 15 can be constructed from any desired material, such as (but not limited to) glass, polymeric material, ceramic material, metal (e.g., stainless steel), or combinations thereof. In some embodiments, the material used to construct barrel 15 can be at least partially transparent to allow the user to monitor mixing of the first and second solutions. The term "transparent" refers to a material property that permits transmission of at least 50% of the light directed at a first side of the material through the other side of the material.

The device barrel can be configured in any desired size, dependent upon the dosage of mixed solution. For example, the barrel can house an internal fluid volume of about 0.5-10 mL. Thus, barrel 5 can have an internal volume of at least about (or no more than about) 0.5, 1, 2, 3, 4, 5, 6, 7, 8, 9, or 10 mL. However, it should be appreciated that the device is not limited, and the barrel can be configured larger or smaller than the range set forth above.

First solution 50 is housed within the interior of barrel 15. First solution 50 can include any solution that can be mixed with a second solution. For example, in some embodiments, the first solution can include a drug, such as a local anesthetic solution. The term "local anesthetic" refers to any anesthetic agent that induces local anesthesia by reversibly inhibiting peripheral nerve excitation and/or transmission. Suitable local anesthetics can comprise any known local anesthetic, including (but not limited to) articaine, bupivacaine, carticaine, cinchocaine/dibucaine, etidocaine, levobupivacaine, lidocaine/lignocaine, mepivacaine, piperocaine, prilocaine, ropivacaine, trimecaine, procaine/benzocaine, chloroprocaine, cyclomethycaine, dimethocaine/larocaine, propoxycaine, procaine/novocaine, proparacaine, tetracaine/amethocaine, lidocaine/prilocaine, saxitoxin, tetrodotoxin, and pharmaceutically acceptable salts thereof. In some embodiments, first solution 50 can include a mixture of more than one solution, such as more than one local anesthetics.

Figure 3A:
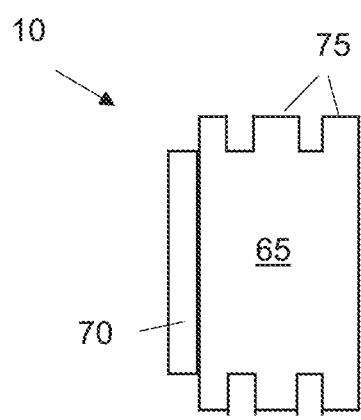
FIGS. 3a and 3b are front plan view of plungers that can be used with the disclosed device in accordance with some embodiments.

As set forth above, plunger 10 is positioned within the interior of barrel 15 and travels from first end 20 to second end 25 to dispense the fluid housed within the device interior. FIG. 3*a* illustrates one embodiment of plunger 10 comprising main body 65 and optional extension 70. The plunger main body has a size and shape that corresponds to the interior of barrel 15 to allow movement from one end to the other. Particularly, the inner diameter of barrel 15 is equal to the outer diameter of main body 65. Thus, if the inner diameter of the barrel is configured with a round cross-sectional shape having a diameter of 0.5 inches, the outer diameter of main body 65 also is configured with a round cross-sectional shape with a diameter of 0.5 inches. In this way, the main body slides in an axial direction through the inside of the barrel to dispense the mixed solution. Further, the plunger main body provides a fluid-tight seal within the interior of the barrel such that fluid cannot leak from the device.

In some embodiments, main body 65 includes one or more ribs 75 positioned about the outer circumference. The ribs function as a sealing ring, ensuring no fluid leaks from the device. Particularly, the ribs are compressed within the tubular barrel, creating a seal that retains fluid within the device interior. The main body can include any number of ribs, such as about 1-5. Further, the ribs can be configured with any desired cross-sectional shape (e.g., square, circular, oval, rectangular). It should be appreciated that ribs 75 are optional, and in some embodiments main body 65 can be configured without ribs.

Figure 3B:
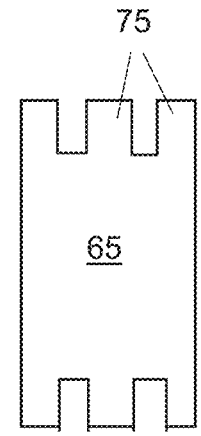

Plunger extension 70 has an outer diameter that is less than the outer diameter of main body 65, as shown. In some embodiments, the outer diameter of the extension can be about 2-50 percent smaller than the outer diameter of the main body. Extension 70 is sized and shaped to cooperate with the interior of cap 30. Particularly, the extension is configured to axially move into the interior of container 30 to dispense fluid from opening 40, as discussed in more detail herein below. Thus, the outer circumference of extension 70 has the same cross-sectional shape and size as the interior of cap 30. It should be appreciated that in some embodiments, extension 70 is optional, as shown in the embodiment of FIG. 3*b*.

Any suitable material can be used to construct plunger 10, such as (but not limited to) rubber, polymeric material, and combinations thereof.

Figure 4A:
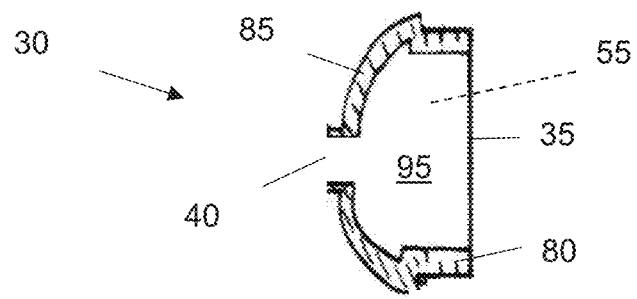
FIGS. 4a and 4b are side plan views of containers that can be used with the disclosed device in accordance with some embodiments.

As discussed above, second end 25 of the device comprises container 30, as illustrated in FIG. 4*a*. Particularly, container 30 comprises neck 80 that is sized and shaped to fit into the interior of barrel 15. Thus, the outer diameter of neck 80 is the same or about the same as the interior diameter of barrel 15. In some embodiments, the outer circumference of neck 80 includes one or more connection elements to allow the container to releasably attach to the barrel. For example, one or more threads 90 can be positioned about the outer circumference of the neck, cooperating with indentations on the interior of barrel 15 at second end 25. However, container 30 can attach to the barrel using any known mechanism, such as mechanical closures (screws, clips, etc.), adhesives, snap-fit engagement, slide fit engagement, and the like.

Container 30 includes interior compartment 95 that houses second solution 55. Second solution 55 can include any solution that can be mixed with first solution 50. For example, in some embodiments, the second solution can include a buffer. The term "buffer" refers to an aqueous solution comprising a mixture of a weak acid and its conjugate base or a weak base and its conjugate acid. In some embodiments, second solution 55 can comprise one or more of sodium bicarbonate, potassium carbonate, calcium carbonate, ammonium carbonate, and magnesium carbonate. Container 30 can house any desired volume of second solution 55, such as (but not limited to) a volume of about 0.1-5 mL. In some embodiments, the ratio of first solution 50 to second solution 55 can be about 1:1 to about 1:20.

Membrane 35 spans the open end of neck 80, adjacent to the interior of the barrel. The term "membrane" as used herein refers to a thin layer of material that separates the interior compartment of container 30 from the interior compartment of barrel 15. Membrane 35 can be constructed from any desired material, including (but not limited to) one or more polymeric materials, metal foil, elastomeric material, and the like. In some embodiments, the membrane can have a thickness of about 2-100 µm. However, it should be appreciated that the thickness of the membrane is not limited and can be configured outside the range set forth above.

In some embodiments, membrane 35 is frangible. The term "frangible" refers to the characteristic of being breakable, such as by force or pressure. Thus, in some embodiments, membrane 35 can have one or more weakened areas (e.g., thinner material, perforations, etc.). In use, membrane 35 is ruptured to allow the contents of the cap and barrel to intermix.

Container 30 further comprises lip 85 that fits over the second end of the barrel, creating a dispensing unit. In some embodiments, the lip has a larger diameter than the outer diameter of barrel 15. The lip includes opening 40 through which the mixed fluid is dispensed. The opening can have any shape that allows fluid to exit container 30. For example, the opening can be straight, as depicted in FIG. 4*a*, or the opening can follow a more tortuous path to allow fluid to be dispensed while resisting the escape of material.

Figure 4B:
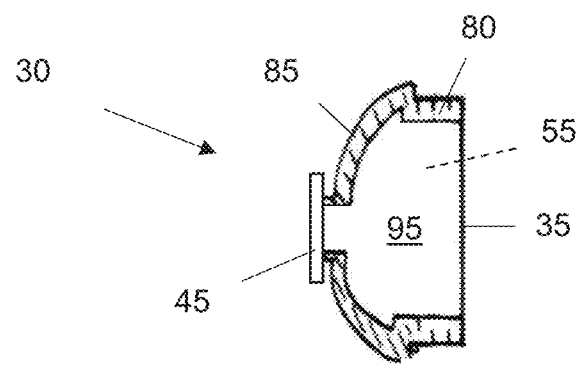

As shown in FIG. 4*b*, cap 45 is positioned over opening 40 to create sealed interior compartment 95. For example, the interior compartment of container 30 can be filled with a desired amount of second fluid 55 through opening 40. The cap is then used to seal the container contents from the outside environment. The cap can further be used as an access point for the insertion of a syringe needle. Cap 45 can be constructed from any desired material, such as (but not limited to) polymeric material, metal foil, and/or elastomeric material.

Container 30 can be constructed from any flexible material. The term "flexible" refers to the characteristic of bending without breaking. In some embodiments, the container can be constructed from one or more polymeric materials, elastomeric material, rubber, and the like.

Figure 5A:
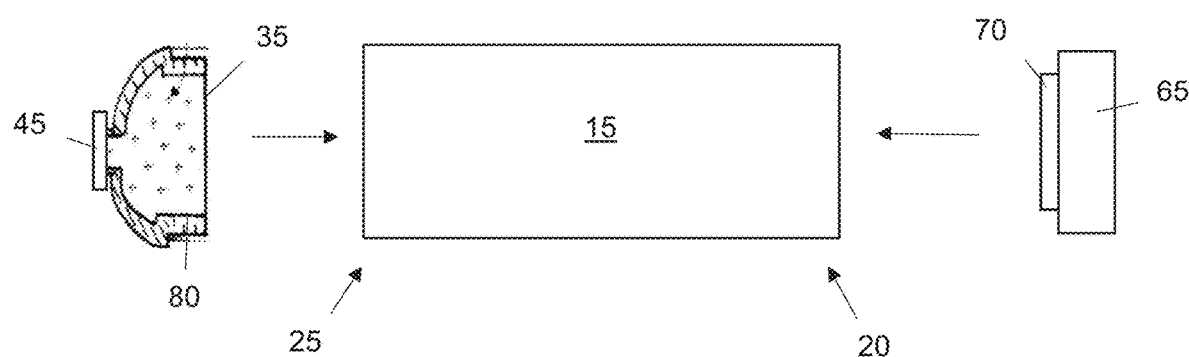
FIGS. 5a and 5b are front plan views of one embodiment of assembling the disclosed device.
Figure 5B:
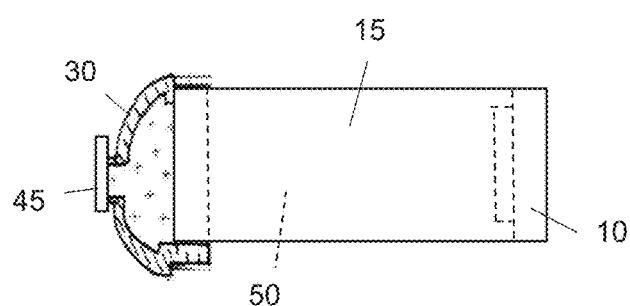

FIGS. 5*a*-5*b* illustrate one method of assembling device 5. As shown, plunger 10 can be positioned within the interior of barrel 15, at first end 20 such that plunger extension 70 faces the interior of the barrel. Container 30 can be positioned on second end 25 of the barrel, such that container membrane 35 faces the interior of the barrel. It should be appreciated that in some embodiments, the container can be initially positioned on barrel 15, followed by positioning of the plunger. Interior compartment 60 of the barrel is filled with a desired amount of first fluid 50 using any known method. For example, after plunger 10 is configured on the first end of the barrel, the fluid can be added, followed by positioning of the container on second end 25 to ensure that the fluid is maintained within the device interior.

In some embodiments, the device of FIG. 5*b* can be deposited into a reusable syringe that includes a rod that manually engages plunger 10. In this way, anesthetic solution is pushed through the entire device. A standard hollow-born needle can be screwed into the metal syringe for stability. One end of the needle pierces cap 45, providing access to the mixed solution (e.g., buffered anesthetic). The second end of the needle can be used to administer the mixed solution into the desired body tissue.

Figure 6A:
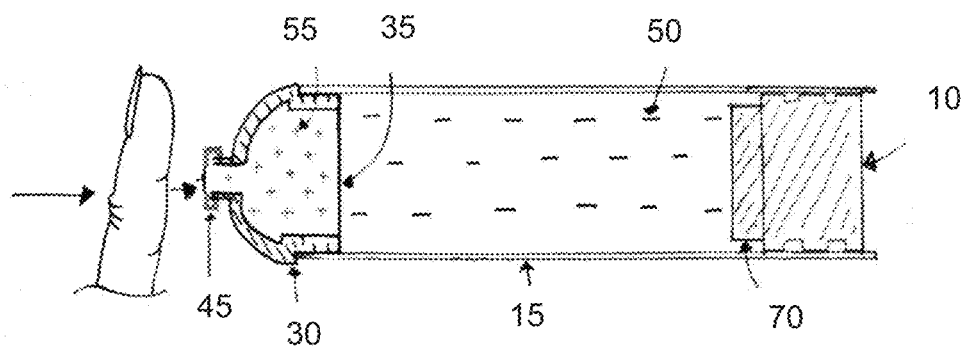
FIGS. 6a and 6b are front plan views of one embodiment of using the disclosed device.
Figure 6B:
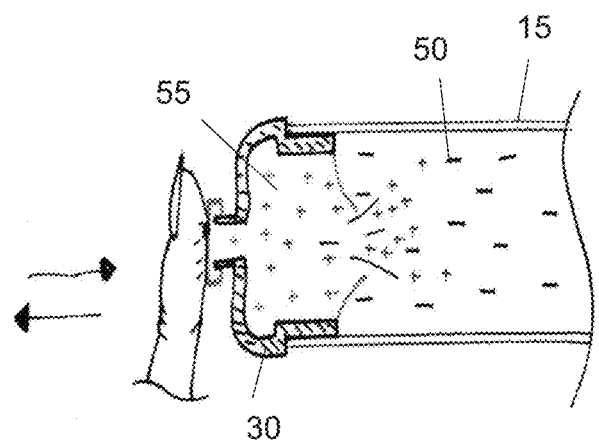

FIGS. 6*a* and 6*b* illustrate one embodiment of the disclosed device during use. As shown, a user applies pressure (such as with a finger) to flexible container 30 at second end 25 of the device. The user manipulates the flexible container towards the interior compartment of barrel 15. As a result, flexible container 30 is deformed, causing an increase in pressure within the container interior. Membrane 35 ruptures from the increased pressure, releasing second solution 55 into the interior of the barrel to intermix with first solution 50. Continuous pumping of the flexible container creates mixing within the interior of the device, as shown in FIG. 6*b*. The user (e.g., physician) can then insert a dispensing needle into membrane of cap 45 to dispense the mixed solution on demand. The plunger is advanced towards second end 25, until extension 70 rests within the interior of compartment 30. The device can then be disposed of.

Figure 7A:
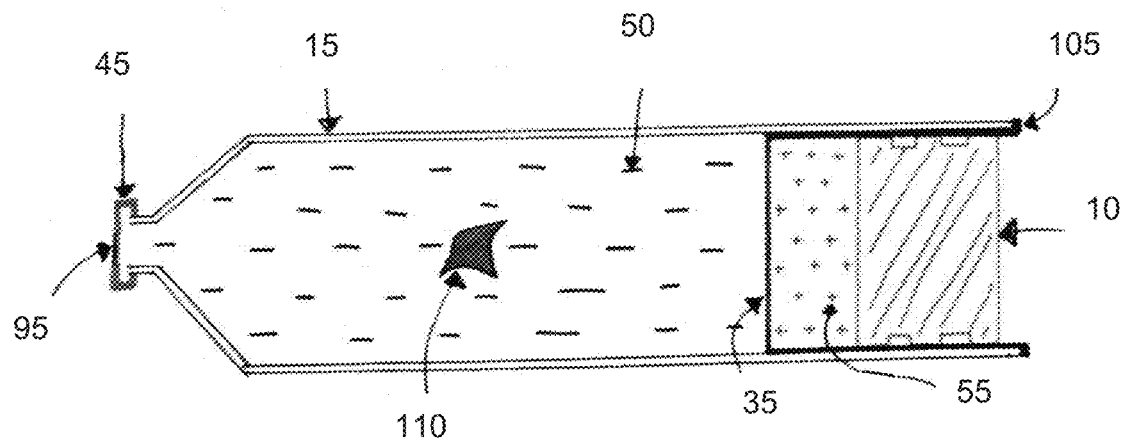
FIG. 7a illustrates a side plan view of a mixing and dispensing device in accordance with some embodiments of the presently disclosed subject matter.

FIG. 7*a* illustrates an alternate embodiment of device 5. As shown, barrel 15 includes a tapered nozzle at second end 25. The nozzle includes opening 40 and cap 45 to allow the interior of the barrel to be filled with a desired amount first fluid 50 (e.g., anesthetic solution). The opening also includes pierceable membrane 95 that allows a user to access the interior of the barrel, such as during dispensing of the mixed fluid. Container 105 houses second fluid 55 (e.g., sodium bicarbonate), and is positioned at first end 20 of the device, between the internal barrel compartment and plunger 10. Container 30 comprises membrane 35, positioned directly adjacent to the interior barrel compartment. Plunger 10 is positioned at first end 20, between container 30 and the external environment. In some embodiments, compartment 30 and plunger 10 can be configured in an insert sleeve to allow for easy insertion into the first end of the barrel. Insert sleeve 105 can be constructed from any desired material, such as polymeric material, metal foil, and the like.

Figure 7B:
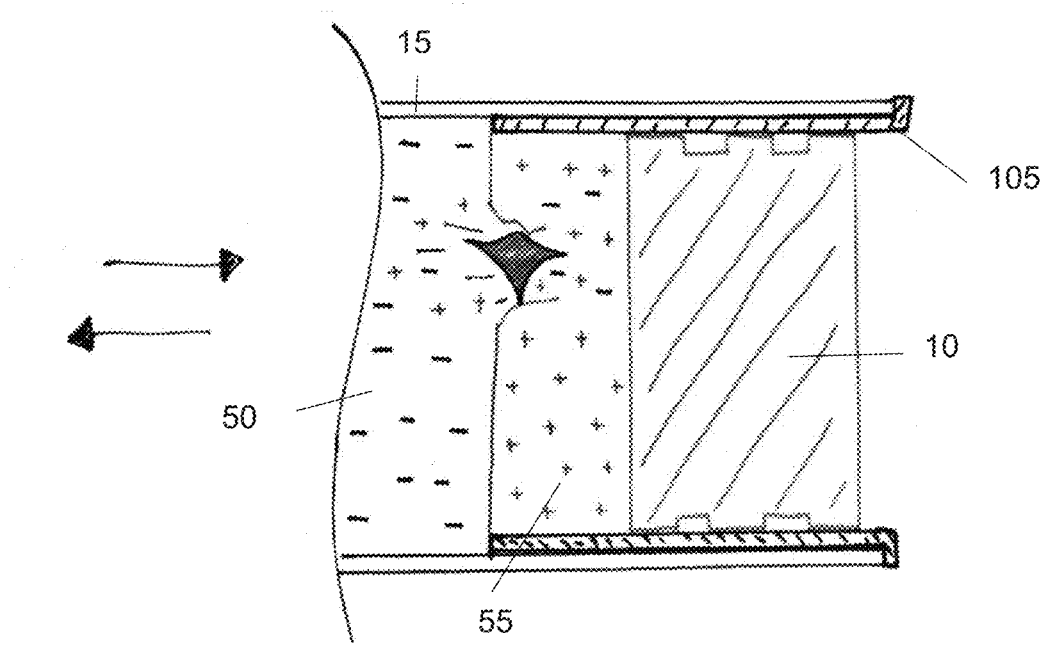
FIG. 7b is a side plan view of the device of FIG. 7a in use.

One or more agitators 110 are dispersed within first fluid 50 or second fluid 55. The term "agitator" as used herein refers to any object capable of piercing membrane 35. In some embodiments, the agitator can be configured as a sharp object, such as an angled piece of plastic or metal. The agitator functions to rupture membrane 35 to allow first and second fluids 50, 55 to intermix. Thus, in use, the user shakes the device to move agitator 110 within the interior of the barrel until it contacts and ruptures membrane 35, as shown in FIG. 7*b*. The user can continue shaking the device until the solutions are intermixed. The user can then advance plunger 10 towards second end 25. In this way, the mixed solution can be dispensed to a patient in need thereof. It should be appreciated that agitator 110 is sized such that it cannot pass through opening 40.

Figure 8A:
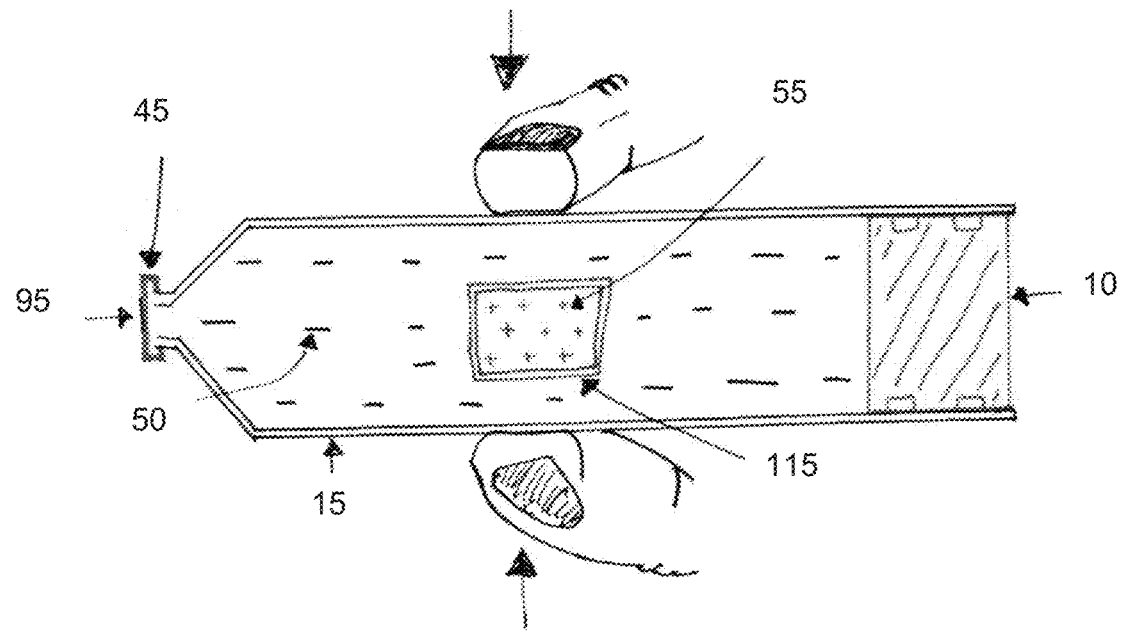
FIG. 8a is a side plan view of a mixing and dispensing device in accordance with some embodiments of the presently disclosed subject matter.
Figure 8B:
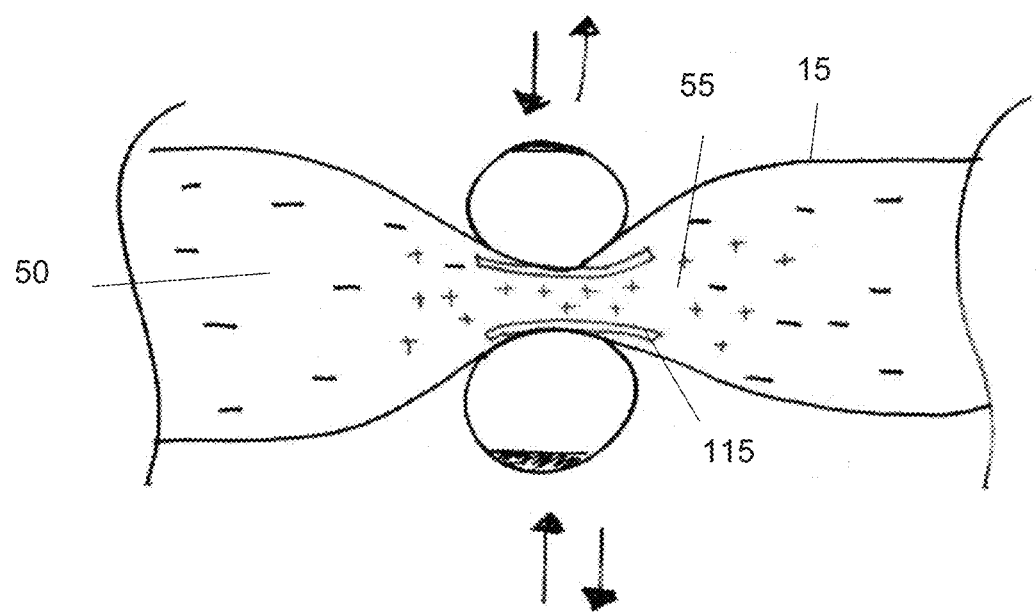
FIG. 8b is a side plan view of the device of FIG. 8a during use.

FIGS. 8*a* and 8*b* illustrate a further embodiment of device 5. As shown, barrel 15 is configured from a flexible material and includes a tapered nozzle at second end 25. The nozzle includes opening 40 and cap 45 to allow the interior of the barrel to be filled with a desired amount first fluid 50 (e.g., anesthetic solution). The opening also includes pierceable membrane 95 that allows a user to access the interior of the barrel, such as during dispensing of the mixed fluid. For example, a user can pierce membrane 100 to cooperatively attach a dispensing needle. Plunger 10 is positioned at first end 20 of the barrel, between the inner barrel compartment and the exterior environment. Second solution 55 (e.g., a buffer) is housed within flexible container 115, positioned within the interior compartment of barrel 15. In some embodiments, the flexible container can be configured as a pouch or other easily manipulatable receptacle.

In use, a user can manipulate the exterior of flexible barrel 15 with the fingers (i.e., through a pinching or squeezing motion) to rupture flexible container 115 housed within the barrel interior, as shown in FIG. 8*b*. In this way, second solution 55 housed within container 115 is intermixed with first solution 50 housed within the barrel interior compartment. The user can then dispense the mixed solution as described herein above.

Figure 9A:
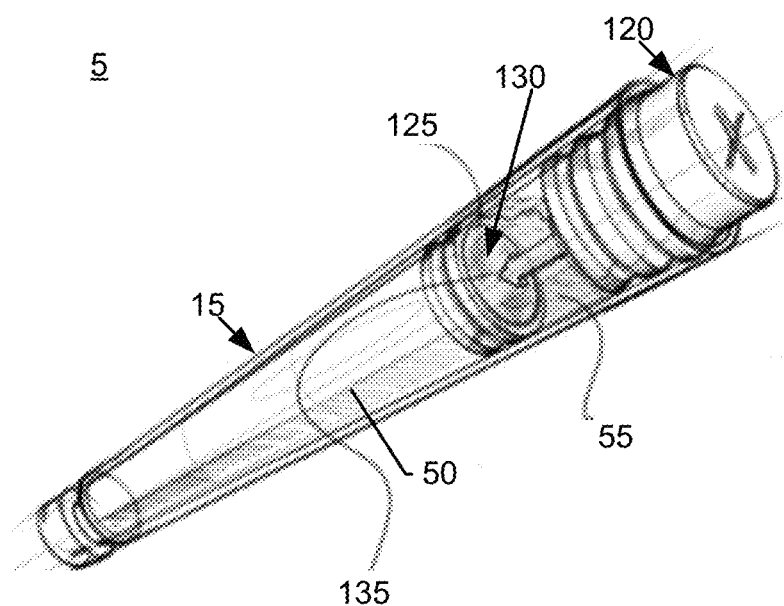
FIG. 9a is a perspective view of a mixing and dispensing device in accordance with some embodiments of the presently disclosed subject matter.
Figure 9B:
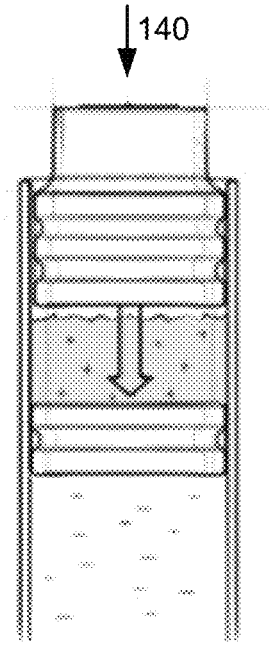
FIGS. 9b-9d are front plan views of one embodiment of using the disclosed device.
Figure 9C:
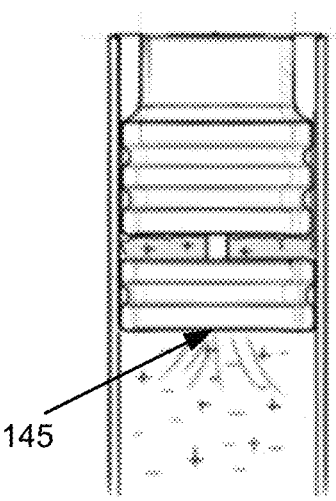
Figure 9D:
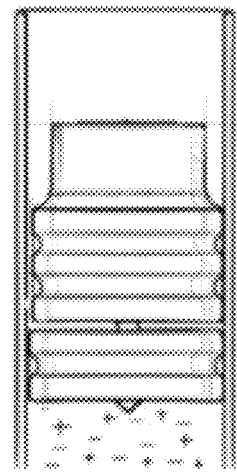

FIG. 9*a* illustrates another embodiment of device 5. A first plunger 120 and a second plunger 125 are sized and positioned to slidably travel within the interior of barrel 15. Particularly, the inner diameter of barrel 15 is equal to the outer diameter of first and second plungers, 120, 125. On one side of second plunger 125, the barrel is filled with a desired amount of first fluid 50 (e.g., anesthetic solution), and between the first and second plungers, 120, 125, the barrel is filled with a desired amount of second fluid 55 (e.g., sodium bicarbonate). First plunger 120 includes a spike or other similar piercing device protruding towards second plunger 125. Second plunger 125 includes a membrane 135 that separates the first fluid 50 from the second fluid 55 within the barrel compartment. Membrane 135 can be constructed from any desired material, including (but not limited to) one or more polymeric materials, metal foil, elastomeric material, and the like. In some embodiments, the membrane can have a thickness of about 2-100 μm. However, it should be appreciated that the thickness of the membrane is not limited and can be configured outside the range set forth above. Membrane 135 may be flexible or frangible and may cover less than the entire cross-sectional area of second plunger 125. In an embodiment, membrane 135 is not necessarily uniform in material or thickness and may include one or more weakened areas comprising perforations, thinner material, or both FIGS. 9*b*-9*d* illustrate operation of the embodiment of FIG. 9*a*. As shown in FIG. 9*b*, when force is applied to the first plunger 120 in the direction shown by arrow 140, such as by a finger, first plunger 120 travels within barrel 15 in the direction shown by arrow 140 toward second plunger 125. As first plunger 120 travels within barrel 15 pressure is applied to second fluid 55 and spike 135 makes contact with and punctures membrane 135. As shown in FIG. 9*c*, as first plunger 120 continues to travel, pressure builds in second fluid 55, forcing it through opening 145 in membrane 135. As second fluid 55 travels through opening 145, second fluid 55 mixes with first fluid 50. Eventually first plunger 120 travels to second plunger 125 and all or nearly all of second fluid 55 is pushed through opening 145 into first fluid 55, where the two fluids mix. At this point, in an embodiment, barrel 15 can be shaken to further mix the first and second fluids 50, 55.

As shown in FIG. 9*d*, first plunger 120 engages second plunger 125 and both the first and second plungers 120, 125, move together in direction 140, which increases pressure in the mixed solution. For depositing the mixed solution into a patient, device 5 of FIGS. 9*a*-9*d*, can be used within a syringe, as part of a syringe, or the mixed fluid can be transferred to a syringe. For example, in an embodiment, device 5 can be incorporated in a standard syringe set up with needle. In another embodiment, the mixed fluid can be drawn out of device 5 by a needle and deposited into a syringe. In another embodiment, device 5 can include the components of a syringe with needle such that a needle and other syringe components can be pre-attached to the device 5 or attached after mixing the solution.

Advantageously, the disclosed system and method allows a user to prepare and intermix two solutions on demand. The user can mix a desired amount of solution, and does not waste excess fluid, thereby providing a cost savings.

Further, the disclosed device enables the user to prepare a mixed solution on demand, thereby optimizing the mixed solution's shelf life.

The disclosed system and method further provide a standardized method of buffering anesthetic directly prior to administering to a patient. The two solutions are pre-measured, thereby reducing the likelihood of measurement errors.

What is claimed is:

1. A device for mixing and delivering a solution, the device comprising:
    a tubular barrel comprising a first end, a second end, and defining an interior space;
    a first plunger positioned near the first end of the barrel and moveable within the interior space of the barrel;
    a first and second compartment defined within the interior space and separated by a membrane; and
    a piercing device movable within the interior space and configured to pierce the membrane when in contact with the membrane;
    wherein the first compartment is configured to house a first solution and the second compartment is configured to house a second solution; and
    wherein, when the first and second solutions are housed:
        the piercing device is freely submersibly positioned within the first compartment and configured to move into contact with and pierce the membrane when an agitating force is applied to the piercing device thereby allowing the first and second solutions to intermix into a mixed solution;
        the first plunger is movable within the barrel to expel the mixed solution through the second end of the barrel.

2. The device of claim 1, wherein when the agitating force is applied to the device, the piercing device moves into contact and pierced the membrane, wherein the agitating force is shaking of the device.

3. The device of claim 1, further comprising a local anesthetic solution as the first solution.

4. The device of claim 3, wherein the local anesthetic solution is selected from one or more of articaine, bupivacaine, carticaine, cinchocaine/dibucaine, etidocaine, levobupivacaine, lidocaine/lignocaine, mepivacaine, piperocaine, prilocaine, ropivacaine, trimecaine, procaine/benzocaine, chloroprocaine, cyclomethycaine, dimethocaine/larocaine, propoxycaine, procaine/novocaine, proparacaine, tetracaine/amethocaine, lidocaine/prilocaine, saxitoxin, tetrodotoxin, and pharmaceutically acceptable salts thereof.

5. The device of claim 1, further comprising a buffer as the second solution.

6. The device of claim 5, wherein the buffer is selected from one or more of sodium bicarbonate, potassium carbonate, calcium carbonate, ammonium carbonate, and magnesium carbonate.

7. The device of claim 1, wherein the first plunger includes a main body with an exterior cross-sectional circumference that is approximately equal to the interior cross-sectional circumference of the barrel and includes one or more sealing ribs.

8. The device of claim 1, wherein at least a portion of the barrel is transparent.

9. The device of claim 1, wherein the pierceable membrane is frangible.

10. The device of claim 1, wherein the pierceable membrane comprises one or more weakened areas comprising perforations, thinner material, or both.

11. The device of claim 1, wherein the device is configured to allow, after mixing the first and second solutions to a mixed solution, the mixed solution to be drawn out of the device by a needle and deposited into a syringe.

12. The device of claim 1, wherein the device further comprises a syringe with needle such that a needle and other syringe components are attachable to the device either before or after mixing the first and second solutions.

13. A method of mixing and delivering a solution, the method comprising:
    housing first and second solutions to be mixed within first and second compartments of a tubular barrel having a first end, a second end, and an interior space with a piercing device and the first and second compartments separated by a membrane;
    moving the piercing device within the interior space to pierce the membrane and allow intermixing of the first and second solutions into a mixed solution, wherein the piercing device is freely submerged within the first solution and an agitating, shaking force is applied to move the piercing device to pierce the membrane; and
    moving a first plunger within the barrel from a first end of the barrel toward the second end to expel the mixed solution through the second end of the barrel.

14. The method of claim 13, wherein the first solution comprises a local anesthetic solution.

15. The method of claim 14, wherein the local anesthetic solution is selected from one or more of articaine, bupivacaine, carticaine, cinchocaine/dibucaine, etidocaine, levobupivacaine, lidocaine/lignocaine, mepivacaine, piperocaine, prilocaine, ropivacaine, trimecaine, procaine/benzocaine, chloroprocaine, cyclomethycaine, dimethocaine/larocaine, propoxycaine, procaine/novocaine, proparacaine, tetracaine/amethocaine, lidocaine/prilocaine, saxitoxin, tetrodotoxin, and pharmaceutically acceptable salts thereof.

16. The method of claim 13, wherein the second solution comprises a buffer.

17. The method of claim 16, wherein the buffer is selected from one or more of sodium bicarbonate, potassium carbonate, calcium carbonate, ammonium carbonate, and magnesium carbonate.

18. The method of claim 13, further comprising attaching a needle to the second end to expel the mixed solution through the needle.

* * * * *